(12) United States Patent
Takeuchi et al.

(10) Patent No.: US 8,338,584 B2
(45) Date of Patent: Dec. 25, 2012

(54) NUCLEIC ACID COMPLEX AND NUCLEIC ACID DELIVERY COMPOSITION

(75) Inventors: Hirofumi Takeuchi, Gifu (JP); Yuichi Tozuka, Gifu (JP); Yasuyuki Hira, Gifu (JP); Hidekazu Toyobuku, Osaka (JP)

(73) Assignees: Otsuka Pharmaceutical Co., Ltd., Tokyo (JP); Hirofumi Takeuchi, Gifu (JP)

( * ) Notice: Subject to any disclaimer, the term of this patent is extended or adjusted under 35 U.S.C. 154(b) by 105 days.

(21) Appl. No.: 12/741,457

(22) PCT Filed: Nov. 6, 2008

(86) PCT No.: PCT/JP2008/070642
§ 371 (c)(1),
(2), (4) Date: Aug. 13, 2010

(87) PCT Pub. No.: WO2009/061003
PCT Pub. Date: May 14, 2009

(65) Prior Publication Data
US 2010/0305190 A1    Dec. 2, 2010

(30) Foreign Application Priority Data
Nov. 8, 2007   (JP) .................................. 2007-291317

(51) Int. Cl.
*C07H 21/04* (2006.01)
*C01H 1/00* (2006.01)
*A61K 31/70* (2006.01)

(52) U.S. Cl. ........................... 536/24.5; 536/1.1; 514/44
(58) Field of Classification Search ........................ None
See application file for complete search history.

(56) References Cited

U.S. PATENT DOCUMENTS
5,827,697 A    10/1998  Takaha et al.
6,248,566 B1    6/2001  Imanaka
2004/0204420 A1 *  10/2004  Rana ............................. 514/251
2006/0030578 A1 *  2/2006  Ahmad et al. ................. 514/283

FOREIGN PATENT DOCUMENTS

| EP | 0 333 490 A2 | 9/1989 |
|---|---|---|
| JP | 8-134104 A | 5/1996 |
| JP | 11-292795 | 10/1999 |
| JP | 3107358 B2 | 9/2000 |
| JP | 2002-529439 A | 9/2002 |
| JP | 2005-508394 A | 3/2005 |
| WO | 00/27795 A1 | 5/2000 |
| WO | 03/040375 A1 | 5/2003 |
| WO | 2004/033620 A2 | 4/2004 |

OTHER PUBLICATIONS

Kogure, Kentaro, et al., "Development of a Non-Viral Multifunctional Envelope-Type Nano Device by a Novel Lipid Film Hydration Method", Journal of Controlled Release, 98 (2004), pp. 317-323.
International Search Report for PCT/JP2008/070642, dated Mar. 25, 2010.

* cited by examiner

*Primary Examiner* — Tracy Vivlemore
(74) *Attorney, Agent, or Firm* — Sughrue Mion, PLLC (57) ABSTRACT

The present invention provides a nucleic acid complex with low toxicity and high safety that can persistently maintain a nucleic acid, such as siRNA or the like, in a cell; and a nucleic acid delivery composition that can efficiently deliver the nucleic acid complex into a cell. A nucleic acid complex with low toxicity and high safety that can persistently maintain a nucleic acid in a cell can be obtained by forming a complex using a nucleic acid to be introduced into a cell, and a highly branched cyclic dextrin. Moreover, when a carrier comprising (A) a diacylphosphatidylcholine, (B) cholesterol and/or a derivative thereof, and (C) an aliphatic primary amine is used as a nucleic acid delivery carrier to introduce the nucleic acid complex into a cell, the safety, the efficiency of intracellular delivery, and the persistence of the nucleic acid in the cell can be further improved.

13 Claims, 2 Drawing Sheets

SEQUENCE LISTING

```
<160> NUMBER OF SEQ ID NOS: 2

<210> SEQ ID NO 1
<211> LENGTH: 19
<212> TYPE: RNA
<213> ORGANISM: Artificial
<220> FEATURE:
<223> OTHER INFORMATION: Sense strand of firefly luciferase
<220> FEATURE:
<221> NAME/KEY: modified base
<222> LOCATION: (19)..(19)
<223> OTHER INFORMATION: Modified by "dTdT"

<400> SEQUENCE: 1
cuuacgcuga guacuucga                                              19

<210> SEQ ID NO 2
<211> LENGTH: 19
<212> TYPE: RNA
<213> ORGANISM: Artificial
<220> FEATURE:
<223> OTHER INFORMATION: Antisense strand of firefly luciferase
<220> FEATURE:
<221> NAME/KEY: modified base
```

```
<222> LOCATION: (19)..(19)
<223> OTHER INFORMATION: Modified by "dTdT"

<400> SEQUENCE: 2
ucgaaguacu cagcguaag                                              19
```

NUCLEIC ACID COMPLEX AND NUCLEIC ACID DELIVERY COMPOSITION

CROSS REFERENCE TO RELATED APPLICATIONS

This application is a National Stage of International Application No. PCT/JP2008/070642 filed Nov. 6, 2008, claiming priority based on Japanese Patent Application No. 2007-291317, filed Nov. 8, 2007, the contents of all of which are incorporated herein by reference in their entirety.

TECHNICAL FIELD

The present invention relates to a nucleic acid complex that can persistently reside in a cell and has low toxicity and high safety, and a composition for nucleic acid delivery.

BACKGROUND ART

With recent developments in biotechnology, a variety of nucleic acids exhibiting physiologically active functions in cells have been discovered. For example, it is known that siRNA (small interfering RNA) causes the degradation of the mRNA of a target gene in a cell, and interferes with the expression of the target gene (RNA interference). The inhibitory function on target gene expression due to such RNA interference is useful for the mitigation or treatment of disease symptoms caused by the abnormal expression of specific genes or gene clusters, and the development of therapeutic agents using siRNA is expected. However, since nucleic acids are water-soluble macromolecules having a negative charge, they have extremely low intracellular gene delivery efficiencies, resulting in inefficient therapeutic effects under gene therapies including siRNA therapies.

Use of a carrier (vector) has been known to efficiently deliver genes into cells. Vectors include viral vectors and non-viral vectors. Viral vectors have high nucleic acid introduction efficiency; however, there are various unknown safety aspects including pathogenicity, immunogenicity and cytotoxicity. Therefore, the use of non-viral vectors is desired for clinical applications.

Examples of non-viral vectors include Lipofectamine™2000, which is already commercially available. Further, a cationic lipid with a specific structure (see, Patent Document 1), and a composition (see, Patent Document 2) containing an amphiphilic compound and a polycation have been reported. Intracellular nucleic acid delivery using a non-viral vector is conducted by first mixing the nucleic acid to be delivered with the non-viral vector to form a complex, and then bringing the complex into contact with the target cell. When a non-viral vector can form a liposome, the vector is incorporated into a cell with a nucleic acid enveloped in the liposome, thereby conducting intracellular nucleic acid delivery.

Nucleic acids such as siRNA, however, have the specific features of poor stability and a strong electric charge. Therefore, the nucleic acid has problematically reduced stability when mixed with a non-viral vector, inhibiting continuous nucleic acid introduction into a cell. Though an example in which a nucleic acid is entrapped in a liposome by forming a complex of the siRNA and the cationic polymer has been known (see, Non-patent Document 1), it is not usable in practice in view of the cytotoxicity of the cationic polymer. Further, even when a stable complex can be formed using a known non-viral vector and a nucleic acid, the complex may have low intracellular delivery ability or may be rapidly delivered into a cell. Therefore, such known non-viral vectors cannot persistently maintain the nucleic acid in the cell; which fails to keep the desired effects obtained by the nucleic acid.

In light of the prior art, the development of techniques for efficiently delivering a nucleic acid (e.g., siRNA) into a cell and for persistently maintaining the nucleic acid with low toxicity and high safety has been desired.

Patent Document 1: Japanese Unexamined Patent Publication No. 2002-529439

Patent Document 2: Japanese Unexamined Patent Publication No. 2005-508394

Non-patent Document 1: Kentaro Kogure et al., Development of a non-viral-multifunctional-envelope-type nano device by a novel lipid film hydration method, J. Control. Release, 98 (2004) 317-323

DISCLOSURE OF THE INVENTION

Problems to be Solved by the Invention

An object of the present invention is to solve the problems of the prior art. Specifically, an object of the present invention is to provide a nucleic acid complex with low toxicity and high safety that can persistently maintain a nucleic acid, such as siRNA or the like, in a cell; and a nucleic acid delivery composition that can efficiently deliver the nucleic acid complex into a cell. Another object of the present invention is to provide a pharmaceutical composition comprising a nucleic acid delivery composition, and a method for delivering a nucleic acid into a cell by bringing a nucleic acid delivery composition into contact with the cell.

Means for Solving the Problems

The present inventors conducted extensive research to solve the above problems, and found that a nucleic acid complex with low toxicity and high safety that can persistently maintain a nucleic acid in a cell can be obtained by forming a complex using the nucleic acid to be introduced into the cell and a highly branched cyclic dextrin. The present inventors further found that the safety, effectiveness of intracellular delivery, and intracellular persistence of a nucleic acid can be further improved by using, as a nucleic acid delivery carrier for introducing the nucleic acid complex into a cell, a carrier comprising (A) a diacylphosphatidylcholine, (B) cholesterol and/or a derivative thereof, and (C) an aliphatic primary amine. The present invention was accomplished by conducting further research based on these findings.

The present invention provides the following items:

Item 1. A nucleic acid complex comprising a nucleic acid and a highly branched cyclic dextrin.

Item 2. The nucleic acid complex according to Item 1, wherein the amount of the highly branched cyclic dextrin is 1 to 4000 parts by weight per part by weight of the nucleic acid.

Item 3. The nucleic acid complex according to Item 1 or 2, wherein the nucleic acid is siRNA.

Item 4. The nucleic acid complex according to any one of Items 1 to 3, wherein the highly branched cyclic dextrin is a glucan with a degree of polymerization of 50 to 5000 having an inner branched cyclic structure portion formed from α-1, 4-glucoside bonds and at least one α-1,6-glucoside bond, and an outer branched structure portion bound to the inner branched cyclic structure portion.

Item 5. The nucleic acid complex according to any one of Items 1 to 4, which is an aggregate obtained by mixing a nucleic acid with a highly branched cyclic dextrin in an aqueous solution.

Item 6. A nucleic acid delivery composition comprising the nucleic acid complex according to any one of Items 1 to 5 and a nucleic acid delivery carrier.

Item 7. The nucleic acid delivery composition according to Item 6, wherein the nucleic acid delivery carrier is a composition comprising (A) a diacylphosphatidylcholine, (B) at least one member selected from cholesterol and derivatives thereof, and (C) an aliphatic primary amine.

Item 8. The nucleic acid delivery composition according to Item 7, wherein Component (A) in the nucleic acid delivery carrier is a diacylphosphatidylcholine in which the acyl moiety has 4 to 23 carbon atoms.

Item 9. The nucleic acid delivery composition according to Item 7, wherein Component (B) in the nucleic acid delivery carrier is cholesterol.

Item 10. The nucleic acid delivery composition according to Item 7, wherein Component (C) in the nucleic acid delivery carrier is an alkylamine having 10 to 20 carbon atoms.

Item 11. The nucleic acid delivery composition according to Item 7, wherein the molar ratio of Components (A):(B):(C) is 5-9:1-5:1.

Item 12. The nucleic acid delivery composition according to Item 7, wherein the nucleic acid delivery carrier is a liposome preparation in which a liposome membrane is formed from Components (A) to (C).

Item 13. A pharmaceutical composition comprising the nucleic acid delivery composition according to any one of Items 6 to 12.

Item 14. The pharmaceutical composition according to Item 13, wherein the nucleic acid is siRNA.

Item 15. Use of the nucleic acid delivery composition according to any one of Items 6 to 12 to produce a pharmaceutical for delivering a nucleic acid into a cell.

Item 16. The use according to Item 15, wherein the nucleic acid is siRNA.

Item 17. A method for delivering a nucleic acid into a cell, the method comprising the step of bringing the nucleic acid delivery composition according to any one of Items 6 to 12 into contact with the cell.

Item 18. The method according to Item 17, wherein the nucleic acid is siRNA.

EFFECTS OF THE INVENTION

The nucleic acid complex of the present invention is obtained by forming a nucleic acid into a complex using a highly branched cyclic dextrin, thereby making it possible for the nucleic acid complex to be highly safe and to be able to stably maintain the nucleic acid in a cell for a long period of time so that useful effects based on the nucleic acid can be persistently exhibited. Further, the nucleic acid complex of the present invention can be readily formed into a complex with a nucleic acid delivery carrier, and can be easily encapsulated even in a nucleic acid delivery carrier in liposome form. The complex of the present invention is therefore also excellent in ease of formulation into a nucleic acid delivery composition. Furthermore, the nucleic acid delivery composition of the present invention can introduce the nucleic acid complex into a cell.

For delivering the nucleic acid complex of the present invention into a cell, the use of a carrier comprising (A) a diacylphosphatidylcholine, (B) cholesterol and/or a derivative thereof, and (C) an aliphatic primary amine, as a carrier for intracellular delivery can increase the efficiency of intracellular delivery of the nucleic acid complex, and can further improve the persistence and safety of such intracellular delivery.

As described above, the nucleic acid complex and nucleic acid delivery composition of the present invention can exhibit useful effects based on the nucleic acid effectively, persistently, and with high safety; therefore, the complex and composition are particularly useful as pharmaceuticals for gene therapy. Thus, the pharmaceutical composition or method of delivering a nucleic acid into a cell according to the present invention can deliver a nucleic acid into a cell more effectively.

BEST MODE FOR CARRYING OUT THE INVENTION

The present invention is described below in detail.

(1) Nucleic Acid Complex

The nucleic acid complex of the present invention comprises a nucleic acid and a highly branched cyclic dextrin.

The nucleic acid used for the nucleic acid complex of the present invention is not limited by the type or structure, as long as it needs to be delivered into the cell. Specific examples of such nucleic acids include siRNA, mRNA, tRNA, rRNA, cDNA, miRNA (microRNA), ribozymes, antisense oligos, decoy oligonucleotides, plasmid DNA, peptide nucleic acids, triplex-forming oligonucleotides (TFOs), aptamers, genes, etc., among which siRNA is preferable. siRNA has the disadvantage of low stability in the presence of heretofore known non-viral vectors, but when siRNA is formed into the nucleic acid complex of the present invention, it has the ability to be continuously delivered into a cell as well as having excellent stability. The nucleic acid used in the nucleic acid complex of the present invention may be derived from humans, animals, plants, bacteria, viruses, or the like, or may be chemically synthesized. Such nucleic acids may be single-stranded, double-stranded, or triple-stranded, and are not limited by the molecular weight. Further, in the present invention, nucleic acids modified with chemicals, enzymes, or peptides can be used. Furthermore, in the present invention, nucleic acids can be used singly or in a combination of two or more.

Figure 1:
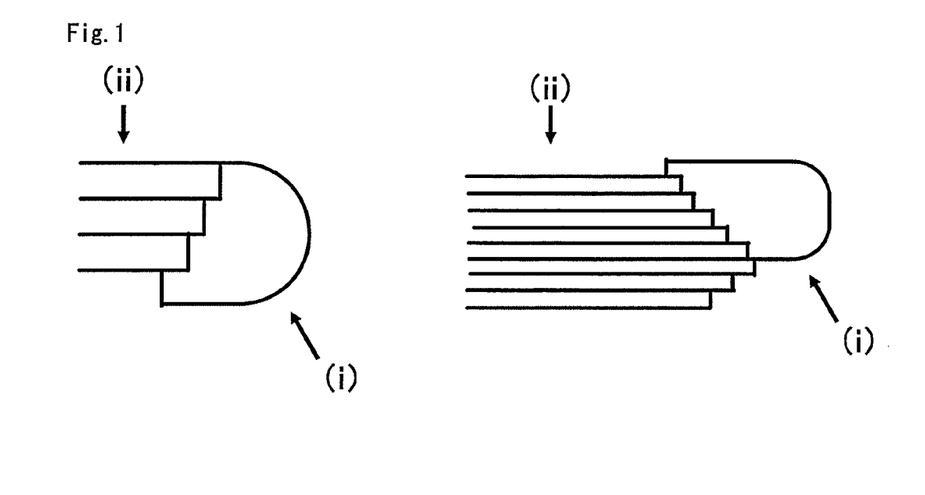
FIG. 1 shows an example of the highly branched cyclic dextrin.

The highly branched cyclic dextrin used in the nucleic acid complex of the present invention is produced by allowing a branching enzyme to act on a saccharide having $\alpha$-1,4-glycoside bonds and at least one $\alpha$-1,6-glycoside bond, such as amylopectin, and is a glucan with a degree of polymerization of 50 to 5000 having an inner branched cyclic structure portion and an outer branched structure portion. The inner branched cyclic structure portion is a cyclic structure portion formed from $\alpha$-1,4-glycoside bonds and at least one $\alpha$-1,6-glycoside bond; and the outer branched structure portion is a non-cyclic structure portion bound to the inner branched cyclic structure portion. The outer branched structure portion is bound to the inner branched cyclic structure portion via at least one $\alpha$-1,6-glycoside bond. Preferable forms of the highly branched cyclic dextrin include the above-mentioned glucan in which the inner branched cyclic structure portion has a degree of polymerization of 10 to 100, the above-mentioned glucan in which the outer branched structure portion has a degree of polymerization of 40 or more, and the above-mentioned glucan in which the unit chains of the outer branched structure portion have an average degree of polymerization of 10 to 20. The highly branched cyclic dextrin can be illustrated as in, for example, FIG. 1 in which the inner branched cyclic structure portion is indicated by (i) and the outer branched structure portion is indicated by (ii).

The degree of polymerization can be determined by gel filtration using a differential refractometer, from the elution position of a material whose degree of polymerization is known. In this determination, the output of a differential refractometer is proportional to the concentration of the glucan, and the output of a low-angle laser light scattering photometer is proportional to the product of the degree of polymerization and concentration of the glucan. Therefore, the degree of polymerization of the glucan can be determined by measuring the ratio of the outputs of the two detectors, i.e., a differential refractometer and a low-angle laser light scattering photometer. The specific conditions are described in U.S. Pat. No. 6,248,566B1 (Japanese Patent No. 3107358).

The highly branched cyclic dextrin and the production process therefor are described in U.S. Pat. No. 6,248,566B1 (Japanese Patent No. 3107358), and the highly branched cyclic dextrin is sold under the registered trademark of "Cluster Dextrin" by Ezaki Glico Co., Ltd.

In the nucleic acid complex of the present invention, the ratio of the highly branched cyclic dextrin to the nucleic acid is not limited, but is usually 1 to 4000 parts by weight, preferably 10 to 1000 parts by weight, and more preferably 100 to 400 parts by weight, of the highly branched cyclic dextrin per part by weight of the nucleic acid. In terms of molar ratio, the above ratio is, for example, 0.1 to 1000 mol, preferably 1 to 100 mol, and more preferably 10 to 20 mol, of the highly branched cyclic dextrin per mol of the nucleic acid. Satisfying such a ratio makes it possible to render more remarkable the continuity of intracellular delivery of nucleic acid by a nucleic acid delivery carrier, and the safety thereof.

The average particle diameter of the nucleic acid complex of the present invention is usually 6 to 60 nm, preferably 8 to 30 nm, and more preferably 10 to 20 nm. The average particle diameter of the nucleic acid complex is measured as a volume average particle diameter using a dynamic laser light scattering method.

The nucleic acid complex of the present invention is a complex formed by aggregation of the nucleic acid and the highly branched cyclic dextrin. The nucleic acid complex of the present invention is produced by mixing the nucleic acid and highly branched cyclic dextrin in a solution that can stably disperse the two compounds. Specific examples of solutions that can stably disperse the nucleic acid and highly branched cyclic dextrin include buffers such as Tris and the like. The buffers may contain chelating agents such as ethylenediaminetetraacetic acid (EDTA) and the like. The conditions for mixing the nucleic acid and the highly branched cyclic dextrin may be such that, in the above-mentioned solution, for example, about 0.1 μM to about 100 μM, preferably about 1 μM to about 10 μM, of the nucleic acid are mixed with about 1 μM to about 1000 μM, and preferably about 10 μM to about 100 μM, of the highly branched cyclic dextrin, at room temperature for about 1 to about 100 minutes, and preferably about 5 to about 10 minutes. The thus produced nucleic acid complex of the present invention is present as a dispersion in the solution. The dispersion can be mixed as it is, or after dilution or concentration if necessary, with a nucleic acid delivery carrier.

(2) Nucleic Acid Delivery Composition

The nucleic acid complex is incorporated into a nucleic acid delivery carrier by being mixed with the nucleic acid delivery carrier, and thereby the nucleic acid is enabled to be delivered into a cell. That is, the present invention also provides a nucleic acid delivery composition comprising the nucleic acid complex and a nucleic acid delivery carrier.

The nucleic acid delivery carrier is a non-viral vector used as a nucleic acid carrier to deliver (introduce) a nucleic acid into a cell. The nucleic acid delivery composition is a composition used for bringing the nucleic acid into contact with the cell into which the nucleic acid is to be delivered, in order to introduce the nucleic acid contained in the composition into the cell.

Formulation of Nucleic Acid Delivery Carrier

The nucleic acid delivery carrier used in the nucleic acid delivery composition of the present invention is not limited as long as it is capable of incorporating a nucleic acid into a cell. Examples of usable nucleic acid delivery carriers include known carriers such as Lipofectamine™2000 and the like.

From the viewpoint of the further improvement of the intracellular persistence of the nucleic acid contained in the nucleic acid complex, and the further improvement of the efficiency and safety of intracellular delivery, it is preferable to use, for example, a carrier comprising (A) a diacylphosphatidylcholine, (B) cholesterol and/or a derivative thereof, and (C) an aliphatic primary amine (hereinafter referred to as "Carrier 1").

The diacylphosphatidylcholine (hereinafter sometimes referred to as "Component (A)") used in Carrier 1 is not limited as long as it is pharmacologically acceptable, and may be, for example, a diacylphosphatidylcholine in which the acyl moiety has 4 to 23 carbon atoms. The carbon numbers of the two acyl groups constituting the diacylphosphatidylcholine may be the same or different.

Specific examples of diacylphosphatidylcholines include dilauroylphosphatidylcholine, dimyristoylphosphatidylcholine, dipalmitoylphosphatidylcholine, distearoylphosphatidylcholine, dioleoylphosphatidylcholine, dilinoleoylphosphatidylcholine, myristoylpalmitoylphosphatidylcholine, myristoylstearoylphosphatidylcholine, palmitoylstearoylphosphatidylcholine, dibutyloylphosphatidylcholine, dihexanoylphosphatidylcholine, diheptanoylphosphatidylcholine, didecanoylphosphatidylcholine, diphthanoylphosphatidylcholine, didodecylphosphatidylcholine, dieicosanoylphosphatidylcholine, dihenicosanoylphosphatidylcholine, dierucoylphosphatidylcholine, diarachidonoylphosphatidylcholine, bis(tricosadinoyl) phosphatidylcholine, etc. Among these, preferable examples include diacylphosphatidylcholines in which the acyl moiety has 12 to 18 carbon atoms; more preferable examples include dimyristoylphosphatidylcholine, dipalmitoylphosphatidylcholine, distearoylphosphatidylcholine, myristoylpalmitoylphosphatidylcholine, myristoylstearoylphosphatidylcholine, palmitoylstearoylphosphatidylcholine, and like diacylphosphatidylcholines in which the acyl moiety has 13 to 17 carbon atoms; particularly preferable examples include dimyristoylphosphatidylcholine, dipalmitoylphosphatidylcholine, and distearoylphosphatidylcholine; and the most preferable examples include distearoylphosphatidylcholine. Such diacylphosphatidylcholines may be used singly or in a combination of two or more.

Cholesterol and/or a derivative thereof (hereinafter sometimes referred to as "Component (B)") used in Carrier 1 is not limited as long as it is pharmacologically acceptable. Derivatives of cholesterol are cationic lipids with a cholesterol skeleton, and specific examples include 3β-[N—(N',N'-dimethylaminoethane)-carbamoyl]cholesterol (DC-Chol), 3β-[N',N',N'-trimethylaminoethane]cholesterol iodide (TC-Chol), bis(guanidinium)-tren-cholesterol (BGTC), N-cholesteryloxycarbonyl-3,7-diazanonan-1,9-diamine, β-alanine-diethanolamine-cholesterol, $N^4$-spermine cholesteryl carbamate (GL-67), N[$N^4$-3-aminopropylspermidine]cholesteryl carbamate (GL-78), $N^4$-spermine cholesteryl carboxamide (GL-90), N1,N8-bis(arginine carboxamide)-$N^4$-spermidine cholesteryl carbamate (GL-95), and N—[$N^1$,$N^4$,$N^8$-tris(3-aminopropyl)spermidine]cholesteryl carbamate (GL-96). Preferable examples of Component (B) include cholesterol. In Carrier 1, cholesterol and derivatives thereof can be used singly or in a combination of two or more as Component (B).

The aliphatic primary amine (hereinafter sometimes referred to as "Component (C)") used in Carrier 1 is not limited as long as it is pharmacologically acceptable, and may be, for example, an alkylamine in which the alkyl moiety has 10 to 20 carbon atoms.

Specific examples of aliphatic primary amines include laurylamine, myristylamine, palmitylamine, stearylamine, oleylamine, decanoylamine, phthanoylamine, etc. Among these, alkylamines in which the alkyl moiety has 12 to 18 carbon atoms are preferable; stearylamine, oleylamine, and palmitoylamine are more preferable; and stearylamine is especially preferable. These aliphatic primary amines may be used singly or in a combination of two or more.

Carrier 1 comprises a combination of Components (A) to (C) described above. In order to further improve the efficiency of intracellular delivery of a nucleic acid, and further reduce the toxicity, the following combinations are preferable: (A) a diacylphosphatidylcholine in which the acyl moiety has 4 to 23 carbon atoms, (B) cholesterol and/or a derivative thereof, and (C) a $C_{10-20}$ alkylamine; and more preferably, (A) dimyristoylphosphatidylcholine, dipalmitoylphosphatidylcholine, and/or distearoylphosphatidylcholine, (B) cholesterol, and (C) stearylamine.

In Carrier 1, the ratio of Components (A) to (C) is not limited, and may be, for example, a Components (A):(B):(C) molar ratio of 5-9:1-5:1, preferably 6-9:1-4:1, and more preferably 7-8:2-3:1. Satisfying such a ratio makes it possible to achieve intracellular nucleic acid delivery with more improved efficiency and lower toxicity.

The total amount of Components (A) to (C) in the total amount of Carrier 1 is, for example, 1 to 100 wt. %, preferably 20 to 90 wt. %, and more preferably 30 to 70 wt. %.

Carrier 1 may contain, in addition to Components (A) to (C), other cationic lipids. Specific examples of usable cationic lipids include squalamine, 3a,7a,12a-tris(3-aminopropoxy)-5β-cholan-24-(N,N-bis(3-aminopropyl)amine), 3a,7a,12a-tris(3-aminopropoxy)-5β-cholan-24-(N—(N-(3-aminopropyl))-3-aminopropyl)amine, 3a,7a,12a-tris(3-azidopropoxy)-5β-cholan-24-(N,N-bis(2-cyanoethyl)amine)), 3a,7a,12a-tris(3-azidopropoxy)-5,3-cholan-24-(N-(benzyloxycarbonyl)-N-(3-hydroxypropyl)amine), and like cationic lipids to which steroids are bound; umbrella-spermine conjugates and like cationic lipids to which cholic acid is bound; cationic lipids to which sterol glycoside is bound; cationic lipids to which steroid saponin is bound; dimethyldioctadecylammonium bromide salt (DDAB), 1,2-dimyristoyl-3-trimethylammonium propane, 1,2-dioleoyl-3-trimethylammonium propane (DOTAP), 1,2-dioleoyl-3-trimethylammonium propane methylsulfate, 1,2-dipalmitoyl-3-trimethylammonium propane, 1,2-distearoyl-3-trimethylammonium propane, N-(1-(2,3-bis(oleoyloxy)propyl)-N,N,N-trimethylammonium hydrochloride (DOTMA), dimyristoyloxypropyl dimethylhydroxyethylammonium bromide salt (DMRIE), dioleoyloxypropyl dimethylhydroxyethylammonium bromide (DORIE), dimethyldidodecylammonium bromide, N-(a-trimethylammonioacetyl)didodecyl-D-glutamine hydrochloride, N-(a-trimethylammonioacetyl)-O,O'-bis-(1H,1H,2H,2H-perfluorodecyl)-L-glutamine hydrochloride, O,O'-didodecanoyl-N-(a-trimethylammonioacetyl)diethanolamine hydrochloride, methylallyl didodecyl ammonium bromide, N-{p-(w-trimethylammoniobutyloxy)benzoyl}-didodecyl-L-glutamine hydrochloride, 9-(w-trimethylammoniobutyl)-3,6-bis(dodecanoyl)carbazole bromide, dimethyl-dioctadecyl ammonium hydrochloride, N-w-trimethylammoniodecanoyl-dihexadecyl-D-glutamine bromide, N-{p-(w-trimethylammoniohexyloxy)-benzoyl}-ditetradecyl-L-glutamine bromide, p-(w-trimethylammoniodecyloxy)-p'-octyloxyazobenzene bromide salt (MC-1-0810), p-{w-(b-hydroxyethyl)dimethyl-ammoniodecyloxy}-p'-octyloxyazobenzene bromide salt (MC-3-0810), O,O',O"-tridodecanoyl-N-(w-trimethyl-ammoniodecanoyl)-tris(hydroxymethyl)aminomethane bromide salt (TC-1-12), 1,2-dilauryl-glycero-3-ethylphosphocholine, 1,2-dimyristoyl-glycero-3-ethylphosphocholine, 1,2-dipalmitoyl-glycero-3-ethylphosphocholine, 1,2-distearoyl-glycero-3-ethylphosphocholine, 1,2-dioleoyl-glycero-3-ethylphosphocholine, 1-palmitoyl-2-oreoyl-glycero-3-ethylphosphocholine, and like quaternary ammonium salt-type cationic lipids; etc.

When Carrier 1 contains a cationic lipid other than Components (A) to (C), the proportion of the cationic lipid is not limited as long as the effects of the present invention are not impaired, and may be, for example, 1 to 10 parts by weight, preferably 2 to 8 parts by weight, and more preferably 4 to 6 parts by weight, per 100 parts by weight of Components (A) to (C) in total.

Carrier 1 may further contain an oily base, if necessary. The addition of an oily base to use its properties enables control of the efficiency of nucleic acid introduction by Carrier 1. For example, when an oily base is added to adjust the specific gravity of Carrier 1, the contact of a cell with Carrier 1 can be controlled, thereby improving the introduction efficiency in vitro. Further, for example, when an oily base with a temperature sensitivity function is added, the core of the nucleic acid carrier can be disintegrated under predetermined temperature conditions to induce fluctuations in the cell surface, thereby improving the nucleic acid introduction efficiency. Furthermore, for example, when an oily base that has an ability to be disrupted by an external stimulus is added, the core of Carrier 1 can be disintegrated by an external stimulus to induce fluctuations in the cell surface, thereby improving the nucleic acid introduction efficiency.

Examples of oily bases that can be added to Carrier 1 include perfluorocarbon, perfluoropentane, perfluorooctyl bromide, perfluorohexane, perfluorotributylamine, soybean oil, refined soybean oil, hydrogenated soybean oil, unsaponified soybean oil, squalene, castor oil, clove oil, sorbitan trioleate, turpentine oil, safflower oil, safflower oil fatty acid, oleic acid, palm oil, rapeseed oil, fusel oil, olive oil, linseed oil, sesame oil, chlorophyll oil, croton oil, bergamot oil, cedar oil, orange oil, fennel oil, eucalyptus oil, corn oil, lavender oil, marjoram oil, lemon oil, cotton seed oil, coconut oil, egg yolk oil, rose oil, pine oil, almond oil, peanut oil, camellia oil, white camphor oil, chamomile oil, cinnamon oil, peppermint oil, esterified corn oil, ginger oil, Roman chamomile oil, snake oil, spearmint oil, sunflower oil, cacao butter, wheat germ oil, zinc oxide oil, hardened oils, hydrogenated vegetable oils, light liquid paraffin, liquid paraffin, medium chain fatty acid triglycerides, mink oil, bitter orange oil, polyoxyethylene castor oil, polyoxyethylene hydrogenated castor oil, polyoxyethylene hydrogenated castor oil 10, polyoxyethylene hydrogenated castor oil 100, polyoxyethylene hydrogenated castor oil 20, polyoxyethylene hydrogenated castor oil 40, polyoxyethylene hydrogenated castor oil 5, polyoxyethylene hydrogenated castor oil 50, polyoxyethylene hydrogenated castor oil 60, polyoxyl 35 castor oil, process oils, etc. Among such oily bases, perfluoropentane is temperature sensitive, and has the property of boiling at 29.5° C. and thereby becoming a gas. Further, perfluorohexane, perfluorooctyl bromide, and perfluorotributylamine have an ability to be disrupted by an external stimulus, and have the property of causing cavitation in the core of Carrier 1 and disintegrating it when receiving an external stimulus such as ultrasonic irradiation.

When an oily base is contained, the proportion thereof is not limited as long as the effects of the present invention are not impaired, and may be, for example, 0.1 to 50 parts by weight, preferably 1 to 30 parts by weight, and more preferably 5 to 20 parts by weight, per 100 parts by weight of Components (A) to (C) in total.

Carrier 1 may further contain a membrane-fusogenic lipid (helper lipid) if necessary. When containing a membrane-fusogenic lipid, Carrier 1 has further improved intracellular nucleic acid delivery efficiency. Examples of such membrane-fusible lipids include dioleoylphosphatidylethanolamine, dioleoylphosphatidylcholine, transphosphatidylphosphatidylethanolamine, 1,2-bis-(10,12-tricosadinoyl)-phosphoethanolamine, 1,2-dielaidoylphosphoethanolamine, 1,2-dihexadecylphosphoethanolamine, 1,2-dihexanoylphosphoethanolamine, 1,2-dilauroylphosphoethanolamine, 1,2-dilinoleoylphosphoethanolamine, 1,2-dimyristoylphosphoethanolamine, 1,2-dioleoylphosphoethanolamine, 1,2-dipalmitoleoylphosphoethanolamine, 1,2-dipalmitoylphosphoethanolamine, 1,2-diphytanoylphosphoethanolamine, 1,2-distearoylphosphoethanolamine, 1-palmitoyl-2-oleoylphosphoethanolamine, 1-palmitoyl-2-(10,12-tricosadinoyl)phosphoethanolamine, 1,2-dioleoylphosphoethanolamine-N-caproylamine, 1,2-dipalmitoylphosphoethanolamine-N-caproylamine, 1,2-dioleoylphosphoethanolamine-N,N-dimethyl, 1,2-dipalmitoylphosphoethanolamine-N,N-dimethyl, 1,2-dipalmitoylphosphoethanolamine-N-dodecanoyl, 1,2-dioleoylphosphoethanolamine-N-dodecanoyl, 1,2-dioleoylphosphoethanolamine-N-dodecanylamine, 1,2-dipalmitoylphosphoethanolamine-N-dodecanylamine, 1,2-dioleoylphosphoethanolamine-N-glutaryl, 1,2-dipalmitoylphosphoethanolamine-N-glutaryl, 1,2-dioleoylphosphoethanolamine-N-lactose, 1,2-dioleoylphosphoethanolamine-N-[4(p-maleimidemethyl)cyclohexane-carboxylate](, dipalmitoylphosphoethanolamine-N-[4(p-maleimidemethyl)cyclohexane-carboxylate], 1,2-dipalmitoylphosphoethanolamine-N-[4(p-maleimidephenyl)butylamide], 1,2-dioleoylphosphoethanolamine-N-[4 (p-maleimidephenyl)butyrate], 1,2-dioleoylphosphoethanolamine-N-methyl, dipalmitoylphosphoethanolamine-N-methyl, 1,2-dioleoylphosphoethanolamine-N-[3-(2-pyridyldithio)propionate], 1,2-dipalmitoylphosphoethanolamine-N-[3-(2-pyridyldithio)propionate], 1,2-dioleoylphosphoethanolamine-N-(succinyl), 1,2-dipalmitoylphosphoethanolamine-N-(succinyl), etc. Among such lipids, dioleoylphosphatidylethanolamine can be advantageously used in Carrier 1.

When such a membrane-fusogenic lipid is contained, the proportion thereof is not limited as long as the effects of the present invention are not impaired, and may be, for example, 1 to 500 parts by weight, preferably 10 to 250 parts by weight, and more preferably 25 to 100 parts by weight, per 100 parts by weight of Components (A) to (C) in total.

Carrier 1 may contain various additives such as isotonizing agents, excipients, diluents, thickeners, stabilizers, buffers, preservatives, etc.; and/or aqueous vehicles such as purified water, aqueous sugar solutions, buffer solutions, physiological saline, aqueous polymer solutions, RNase free water, etc.; according to the form of use. The amounts of such additives and aqueous vehicles to be added can be suitably selected according to the form of use of the nucleic acid delivery carrier.

Form of Nucleic Acid Delivery Carrier

The form of the nucleic acid delivery carrier is not limited as long as the nucleic acid to be delivered into a cell can be encapsulated, but is preferably in the form of a liposome. For example, when Carrier 1 is in the form of a liposome, Components (A) to (C), and optionally used other lipids, form a liposome membrane.

When the nucleic acid delivery carrier is in the form of a liposome, it may be a small unilamellar vesicle (SUV), a large unilamellar vesicle (LUV), or a multilamellar vesicle (MLV). The particle diameter of the nucleic acid delivery carrier can be suitably selected according to the type of the cell into which the nucleic acid is delivered, and may be, for example, about 20 to about 100 nm for SUV, about 200 to about 1000 nm for LUV, and about 400 to about 3500 nm for MLV. The particle diameter of the liposome is measured using a dynamic laser light scattering method.

Methods known in the art can be used to produce the liposome and adjust the particle diameter of the liposome. For example, in the case of Carrier 1, a liposome can be formed by a thin film method, a reversed phase evaporation method, an ether injection method, a surfactant method, and a heating method, or the like, using an oil phase containing Components (A) to (C) and an aqueous phase (aqueous vehicle). The particle diameter can be adjusted by an extrusion method, a French press method, a homogenization method, or the like.

Form, Formulation, and Method of Use of the Nucleic Acid Delivery Composition

When the nucleic acid delivery carrier is in the form of a liposome, the nucleic acid complex in the nucleic acid delivery composition of the present invention may be present in a state encapsulated within the internal aqueous phase of the liposome, or in a state bound to the inner or outer surface of the liposome membrane by an ionic or hydrophobic bond. When the nucleic acid delivery carrier is in a form other than a liposome, the nucleic acid complex in the nucleic acid delivery composition of the present invention forms a complex with components of the nucleic acid delivery carrier through an ionic or hydrophobic bond.

The nucleic acid delivery composition of the present invention is produced by mixing the nucleic acid complex with the nucleic acid delivery carrier and formulating the mixture into a desired form, or by mixing the components of the nucleic acid complex and the nucleic acid delivery carrier composition in an arbitrary order and formulating the mixture into a desired form.

In the nucleic acid delivery composition of the present invention, the ratio of the nucleic acid complex to the nucleic acid delivery carrier depends on the type of the nucleic acid complex, the type of the nucleic acid delivery carrier, and the type of the cell into which the nucleic acid is delivered, etc. The ratio may be, for example, 1 to 100 parts by weight, preferably 10 to 100 parts by weight, and more preferably 20 to 100 parts by weight, of the nucleic acid complex per 100 parts by weight of the total amount of the nucleic acid delivery carrier. More specifically, when Carrier 1 is used as the nucleic acid delivery carrier, the ratio may be, for example, 1 to 100 parts by weight, preferably 10 to 100 parts by weight, and more preferably 20 to 100 parts by weight, of the nucleic acid complex per 100 parts by weight of the total amount of Components (A) to (C) contained in Carrier 1.

Further, when Carrier 1 is used as the nucleic acid delivery carrier, the total amount of Components (A) to (C) contained in Carrier 1 may be, for example, 10 to 90 wt. %, preferably 30 to 80 wt. %, and more preferably 40 to 60 wt. %, relative to the total amount of the nucleic acid delivery composition.

The nucleic acid delivery composition of the present invention may contain various additives such as isotonizing agents, excipients, diluents, thickeners, stabilizers, buffers, preservatives, etc.; and/or aqueous vehicles such as purified water, aqueous glucose solutions, buffer solutions, physiological saline, etc.; according to the form of use. The amounts of such additives and aqueous vehicles can be suitably selected according to the form of use of the nucleic acid delivery composition.

The nucleic acid delivery composition of the present invention can be used by itself as a pharmaceutical for gene therapy, i.e., as a pharmaceutical composition. When the nucleic acid delivery composition of the present invention is used as a pharmaceutical composition, a nucleic acid delivery carrier, base, vehicle, etc. that are pharmacologically acceptable are selected. The pharmaceutical composition of the present invention may be formulated into various pharmaceutical forms. Examples of the form of the pharmaceutical composition of the present invention include liquid preparations such as solutions (including syrups and the like), drops, injections, etc.; and solid preparations such as tablets, pills, powders, granules, capsules (including soft capsules), etc. When the pharmaceutical composition of the present invention is a liquid preparation, it can be preserved by freezing or by lyophilization or the like to remove water. Lyophilized preparations, dry syrups, etc. may be re-dissolved at the time of use in distilled water for injection, sterilized water, etc. When the pharmaceutical composition of the present invention is a solid preparation, it may be re-dissolved at the time of use in distilled water for injection, sterilized water, etc.

In the present invention, the cell into which a nucleic acid is delivered, i.e., the cell to which the pharmaceutical composition of the present invention is applied, is not limited, and may be a cultured cell, a cell isolated from an organism (including established cell lines), a cell in vivo, etc., and may be derived from a human or a non-human animal. The pharmaceutical composition of the present invention may be applied either in vitro or in vivo.

In the present invention, a nucleic acid can be delivered into a cell through the step of bringing the pharmaceutical composition of the present invention into contact with the cell. The method for bringing the pharmaceutical composition into contact with a cell is not limited, as long as a suitable amount of the nucleic acid delivery composition is brought into contact with the cell into which the nucleic acid is to be introduced. For example, the method may be the same as a hitherto known method in gene therapy, and the same applies to the amount to be brought into contact: the method and amount are suitably selected. Thus, application of the pharmaceutical composition of the present invention to a cell enables easy intracellular delivery of a nucleic acid, and maintains the delivered nucleic acid stably and persistently in the cell.

For example, to bring the pharmaceutical composition of the present invention into contact with a cell in vitro, the cell can be cultured in the presence of a suitable amount of the pharmaceutical composition. To bring the pharmaceutical composition of the present invention into contact in vitro with a cultured cell or a cell isolated from an organism, the contact can be carried out in the presence of blood serum. When the pharmaceutical composition of the present invention is brought into contact with a cell in vivo, the pharmaceutical composition of the present invention may be brought into contact with the cell by, for example, direct injection into a tissue; intravenous, subcutaneous, intramuscular, interperitoneal, or intraocular injection, or injection into the digestive tract, a tooth, or the like; inhalation administration to the nasal cavity, oral cavity, lungs, or the like; oral administration; transdermal administration; transmucosal administration via the oral mucosa, vaginal mucosa, ocular mucosa, rectal mucosa, or uterine mucosa; or the like.

The pharmaceutical composition of the present invention may further comprise, if necessary, a pharmacologically acceptable vehicle or base. The vehicle and base are not limited as long as the effects of the present invention are not impaired, and are suitably selected according to the form of use. Examples include those mentioned above. In this case, the proportions of the pharmaceutical composition, vehicle, and base are also not limited as long as the effects of the present invention are not impaired, and are suitably selected according to the form of use.

In applying the pharmaceutical composition of the present invention, an effective amount thereof is applied. For example, the pharmaceutical composition is applied in such an amount that the nucleic acid complex contained therein is applied in an amount of 0.001 to 10 pM, preferably 0.001 to 1 pM, and more preferably 0.01 to 0.1 pM, per cell.

The pharmaceutical composition of the present invention is capable of delivering a specific nucleic acid into a cell. That is, the pharmaceutical composition of the present invention is effective in delivering into a cell a specific nucleic acid that is present in the pharmaceutical composition and that forms the nucleic acid complex, by bringing the pharmaceutical composition into contact with the cell.

The present invention also provides a method for delivering a nucleic acid into a cell. The method for delivering a nucleic acid into a cell according to the present invention comprises the step of bringing the nucleic acid complex or nucleic acid delivery composition described above into contact with the cell. The contact between the nucleic acid complex or nucleic acid delivery composition and the cell is not limited, as long as a suitable amount of the nucleic acid complex or nucleic acid delivery composition is brought into contact with the cell into which a nucleic acid is introduced. For example, the contact may be carried out in the same manner as a hitherto known method in gene therapy, and the same applies to the amount to be brought into contact: the manner and amount of contact are suitably selected.

By bringing the nucleic acid complex or nucleic acid delivery composition into contact with a cell in the above manner, the nucleic acid can be stably and persistently maintained in the cell. For contact with the cell, the nucleic acid complex may be used by itself or in combination with a vehicle or base as described above. The nucleic acid delivery composition may also be used by itself or in combination with a vehicle or base as described above. For more efficient intracellular nucleic acid delivery, it is preferable to bring the nucleic acid delivery composition into contact with the cell.

In the present invention, as mentioned above, the cell into which a nucleic acid is delivered is not limited, and may be a cultured cell, a cell isolated from an organism (including established cell lines), a cell in vivo, or the like, and may be derived from a human or a non-human animal. The above-mentioned contact may be carried out in vitro or in vivo.

For example, to bring the nucleic acid complex or nucleic acid delivery composition into contact with a cell in vitro, the cell can be cultured in the presence of a suitable amount of the nucleic acid complex or nucleic acid delivery composition. To bring the nucleic acid complex or nucleic acid delivery composition into contact in vitro with a cultured cell or a cell isolated from an organism, the contact can be carried out in the presence of blood serum. When the nucleic acid complex or nucleic acid delivery composition is brought into contact with a cell in vivo, the nucleic acid complex or nucleic acid delivery composition may be brought into contact with the cell by, for example, direct injection into a tissue; intravenous, subcutaneous, intramuscular, interperitoneal, or intraocular injection, or injection into the digestive tract, a tooth, or the like; inhalation administration to the nasal cavity, oral cavity, lungs, or the like; oral administration; transdermal administration; transmucosal administration via the oral mucosa, vaginal mucosa, ocular mucosa, rectal mucosa, or uterine mucosa; or the like.

In the method for nucleic acid delivery into a cell according to the present invention, an effective amount of the nucleic acid complex or nucleic acid delivery composition is brought into contact with a cell to introduce the nucleic acid into the cell. For example, the amount of the nucleic acid complex or nucleic acid delivery composition to be administered is selected so that 0.001 to 10 pM, preferably 0.001 to 1 pM, and more preferably 0.01 to 0.1 pM, of the nucleic acid complex is administered per cell.

The method of delivering a nucleic acid into a cell according to the present invention may be performed by bringing the pharmaceutical composition into contact with the cell. When using the pharmaceutical composition, the method of the present invention can be carried out in the same manner as described above.

EXAMPLES

The invention will now be described in detail based on Examples and the like, but the invention is not limited thereto. In the following Examples and Test Examples, GL3-siRNA (siRNA to firefly luciferase; Dharmacon Research, Inc., (Boulder, Colo.), USA; sense: 5'-CUUACGCUGAGUACU-UCGATT, (SEQ ID NO:1)antisense: 5'-CU-UACGCUGAGUACUUCGATT (SEQ ID NO:2) was used as siRNA. Cluster dextrin (Ezaki Glico Co., Ltd.) was used as the highly branched cyclic dextrin.

Example 1

Preparation of Complex Containing siRNA and Highly-Branched Cyclic Dextrin

A solution containing siRNA in a 2 µM concentration (siRNA solution) was prepared using a Tris-EDTA (TE) buffer solution (produced by Fluka Co., Ltd. Further, a solution containing highly-branched cyclic dextrin in a 25 µM concentration (highly-branched cyclic dextrin solution) was prepared using a Tris-EDTA (TE) buffer solution (produced by Fluka). An equal amount of these solutions were mixed for one minute to form a siRNA complex. Table 1 shows properties of the siRNA complex obtained.

TABLE 1

|  | Particle Diameter (nm) | Zeta Potential (mV) |
|---|---|---|
| Complex | 31.1 | −42.9 |

The particle diameter shown is a mean particle diameter (nm) measured using a ZETASIZER 3000HSA (MALVERN INSTRUMENT) (the volume mean particle diameter was measured using a laser diffraction method). Zeta potential was measured using a ZETASIZER 3000HSA (MALVERN INSTRUMENT).

Example 2

Preparation of siRNA Complex-Containing Nucleic Acid Delivery Composition

Distearoylphosphatidylcholine (DSPC), cholesterol, and stearylamine were weighed out in a molar ratio of 7:3:1, and dissolved in chloroform using an eggplant-type flask (recovery flask). The solution was dried under reduced pressure using a rotary evaporator to form a lipid thin membrane layer. The solution containing 0.028 mg/ml of a siRNA complex obtained in Example 1 was added to the resulting lipid thin membrane layer so that the solution had a DSPC concentration of 30 mg/mL, and then mixed. Thereafter, the particle diameter of the solution was adjusted by passing through membranes having pore diameters of 800 nm and 200 nm using an extruder, to prepare a composition for siRNA delivery in a cationic liposome form. The resulting composition for siRNA delivery had a particle diameter of about 200 nm, and was in a liposome form in which the particles had a uniform particle size. The composition had a zeta potential of about 50 mV. The particle diameter shown is a mean particle diameter (nm) measured using a ZETASIZER 3000HSA (MALVERN INSTRUMENT) (the volume mean particle diameter was measured using a laser diffraction method). Zeta potential was measured using a ZETASIZER 3000HSA (MALVERN INSTRUMENT).

Example 3

Preparation of siRNA Complex-Containing Nucleic Acid Delivery Composition

A nucleic acid delivery composition in a cationic liposome form was prepared in the same manner as in Example 2, except that the ratio of DSPC, cholesterol, and stearylamine was 7:3:2. As in Example 2, the resulting composition for siRNA delivery had a particle diameter of about 200 nm, and was in a liposome form in which the particles had a uniform particle size. The composition had a zeta potential of about 50 mV.

Test Example 1

Evaluation of Inclusion Efficiency of siRNA

A FITC-labeled siRNA complex was prepared in the same manner as in Example 1 above, using FITC pre-labeled siRNA. Using the FITC-labeled siRNA complex, a nucleic acid delivery composition in a cationic liposome form was prepared under the same conditions as in Examples 2 and 3. The siRNA delivery composition immediately after preparation was precipitated by centrifugation (at 75,000 rpm for 1 hour), and the fluorescence intensity of FITC-labeled siRNA present in its supernatant was measured to calculate the siRNA inclusion efficiency (a rate (%) of siRNA enveloped in the liposome to the total siRNA).

As a result, the inclusion efficiency of siRNA indicated high levels of 97.2% when prepared under the same conditions as Example 2, and 99.8% when prepared under the same conditions as Example 3. This reveals that the nucleic acid complex of the invention has the feature of being efficiently introduced into a carrier for nucleic acid delivery in a liposome form. Although a restrictive interpretation is not desired, this is presumably because highly-branched cyclic dextrin forms a compact complex with siRNA.

Test Example 2

Evaluation Test of Cellular Safety

An evaluation was conducted using an MTS assay. A CellTiter 96 Aqueous One Solution Cell Proliferation Assay produced by Promega Corporation was used for the MTS assay. Specifically, A594 cells (ATCC, USA) were inoculated at $3.16 \times 10^4$ cells/well into 200 µl of Dulbecco's Modification of Eagle's Medium (DMEM) containing 10 vol % of fetal bovine serum (FBS) in a 96-well plate, and incubated at 37° C. for 24 hours. After rinsing with Hank's Balanced Salt Solution (HBSS) three times, the medium was changed to DMEM without FBS. Each of the nucleic acid delivery compositions was added in an amount of 20 μl per well and incubated at 37° C. under 5% $CO_2$ for 4 hours. Next, the culture supernatant in the wells was changed to DMEM with 10 vol % of FBS and incubated at 37° C. under 5% $CO_2$ for 20 hours again. Twenty of an MTS (tetrazolium salt) reagent and 100 μl of a DMEM medium with 10 vol % of FBS were added to each well, and incubated for two hours. The absorbance at 492 nm was then determined, and cell viability was calculated. The cell viability was calculated by setting the absorbance at 492 nm determined without adding the nucleic acid delivery composition, which was incubated under the above conditions, as 100%.

Figure 2:
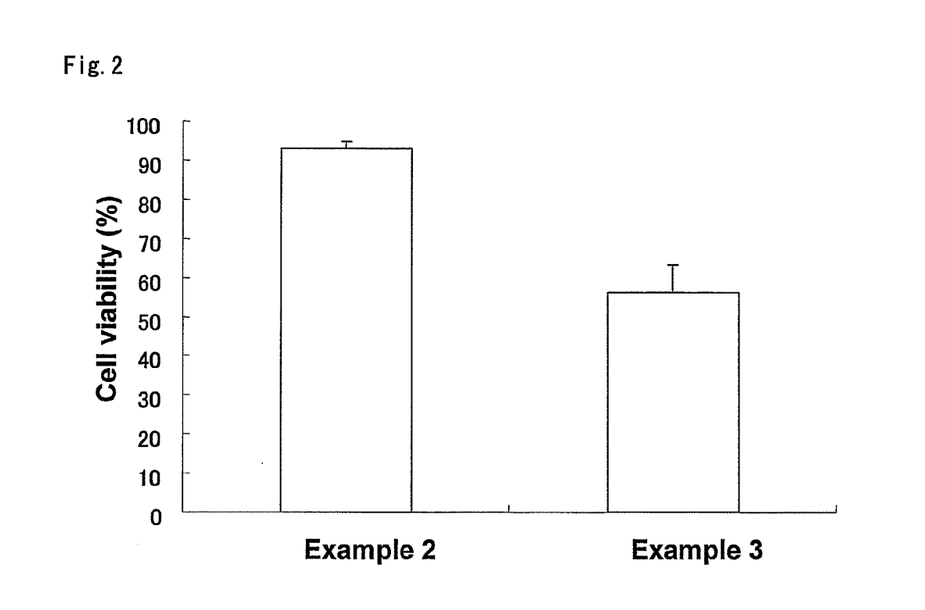
FIG. 2 shows the results of Test Example 2, i.e., the results of the evaluation of the nucleic acid delivery compositions for cellular safety.

FIG. 2 shows the results. As shown in FIG. 2, it became apparent that all nucleic acid delivery compositions of Examples 2 and 3 have low cytotoxicity and are highly safe. Particularly, it was confirmed that the nucleic acid delivery compositions of Examples 2 and 3 showed a significant high level of safety.

Test Example 3

Evaluation Test of siRNA Delivery Efficiency into Cells

The intracellular introduction efficiency of siRNA was evaluated by measuring the fluorescence intensity of FITC-labeled siRNA using flow cytometry. In this test, a nucleic acid delivery composition prepared with FITC pre-labeled siRNA was used. Specifically, A594 cells (ATCC, USA) were inoculated at 5×10⁵ cells/well into 500 μl of DMEM with 10 vol % of FBS in a 24-well plate, and incubated at 37° C. under 5% $CO_2$ for 24 hours. After rinsing three times with HBSS, 0.95 ml of DMEM containing no FBS was added. 0.05 ml of each of the nucleic acid delivery compositions of Examples 1 and 2 were further added to each well, and incubated at 37° C. under 5% $CO_2$ for 4 hours. Next, the culture supernatant in the wells was changed to DMEM with 10 vol % of FBS and incubated at 37° C. under 5% $CO_2$ for 20 hours again. Each well was rinsed with HBSS once, and 0.2 ml of CellScrub-Buffer (produced by Gene Therapy Systems, Inc.) was added. Incubation was conducted at 37° C. under 5% $CO_2$ for 15 minutes. Again, the wells were rinsed with HBSS twice, and cells attached to the well bottom were detached using trypsin and collected by centrifugation. The resulting cells were suspended in HBSS. The suspension was filtered through a membrane having a pore diameter of 41 μm. The fluorescence intensity of the cells was measured using flow cytometry at 2 hours, 12 hours and 24 hours after the addition of the nucleic acid delivery compositions. As a control, the fluorescence intensity of the cells was measured in the same manner as described above, using a control nucleic acid delivery composition obtained by mixing a solution of Lipofectamine 2000™ (produced by Invitrogen Corporation), often used as a commercially-available gene vector, diluted with Opti-MEM media to 0.1 mg/mL, and a siRNA solution in which siRNA was diluted with TE buffer at a concentration of 2 μM in a volume ratio of 1:1.

Figure 3:
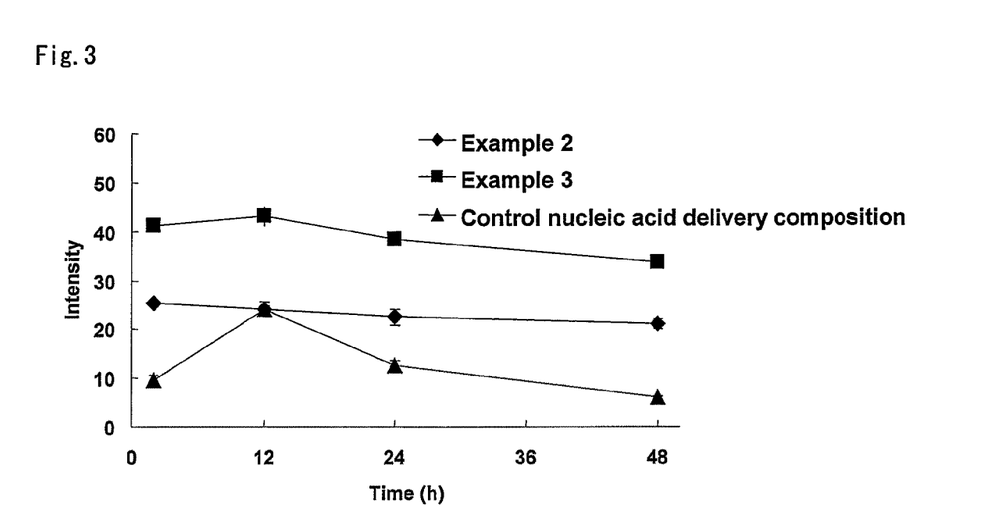
FIG. 3 shows the results of the evaluation of siRNA introduction into cells mediated by each nucleic acid delivery composition in Test Example 3. The ordinate in FIG. 3 indicates the average fluorescence intensity per one cell.

FIG. 3 shows the results. It was confirmed from the results that siRNA was persistently maintained, with its concentration kept constant in the cells in any of the cases for the nucleic acid delivery compositions of Examples 1 and 2. Contrarily, the control nucleic acid delivery compositions showed not only low initial siRNA intracellular delivery efficiency, but also a decrease in intracellular siRNA with time, resulting in insufficient amounts of siRNA in the cells at 12 hours, and 24 hours after addition.

The invention claimed is:

1. A nucleic acid complex comprising a nucleic acid and a highly branched cyclic dextrin, wherein said highly branched cyclic dextrin is a glucan with a degree of polymerization of 50 to 5000 having an inner branched cyclic structure portion formed from α-1,4-glucoside bonds and at least one α-1,6-glucoside bond, and an outer branched structure portion bound to the inner branched cyclic structure portion.

2. The nucleic acid complex according to claim 1, wherein the amount of the highly branched cyclic dextrin is 1 to 4000 parts by weight per part by weight of the nucleic acid.

3. The nucleic acid complex according to claim 1, wherein the nucleic acid is siRNA.

4. The nucleic acid complex according to claim 1, which is an aggregate obtained by mixing said nucleic acid with said highly branched cyclic dextrin in an aqueous solution.

5. A nucleic acid delivery composition comprising the nucleic acid complex according to claim 1 and a nucleic acid delivery carrier.

6. The nucleic acid delivery composition according to claim 5, wherein the nucleic acid delivery carrier is a composition comprising (A) a diacylphosphatidylcholine, (B) at least one member selected from cholesterol and derivatives thereof, and (C) an aliphatic primary amine.

7. The nucleic acid delivery composition according to claim 6, wherein Component (A) in the nucleic acid delivery carrier is a diacylphosphatidylcholine in which the acyl moiety has 4 to 23 carbon atoms.

8. The nucleic acid delivery composition according to claim 6, wherein Component (B) in the nucleic acid delivery carrier is cholesterol.

9. The nucleic acid delivery composition according to claim 6, wherein Component (C) in the nucleic acid delivery carrier is an alkylamine having 10 to 20 carbon atoms.

10. The nucleic acid delivery composition according to claim 6, wherein the molar ratio of Components (A):(B):(C) is 5-9:1-5:1.

11. The nucleic acid delivery composition according to claim 6, wherein the nucleic acid delivery carrier is a liposome preparation in which a liposome membrane is formed from Components (A) to (C).

12. A pharmaceutical composition comprising the nucleic acid delivery composition according to claim 5.

13. A method for delivering a nucleic acid into a cell, the method comprising the step of bringing the nucleic acid delivery composition according to claim 5 into contact with the cell.

* * * * *